US007045579B2

(12) United States Patent
Van Den Berg et al.

(10) Patent No.: US 7,045,579 B2
(45) Date of Patent: May 16, 2006

(54) COATING COMPOSITION COMPRISING AN ACETAL-FUNCTIONAL BINDER

(75) Inventors: Keimpe Jan Van Den Berg, Sassenheim (NL); Klaus Hobel, Oosterbeek (NL); Josephus Christiaan Van Oorschot, Arnhem (NL); Marcel Johannes Antonius Mensink, Arnhem (NL); Kenny Abdoel Nassier Raghosing, Castricum (NL); Edith Hulsbos, Woerden (NL)

(73) Assignee: Akzo Nobel N.V., Arnhem (NL)

( * ) Notice: Subject to any disclaimer, the term of this patent is extended or adjusted under 35 U.S.C. 154(b) by 115 days.

(21) Appl. No.: 10/383,600

(22) Filed: Mar. 7, 2003

(65) Prior Publication Data

US 2003/0207104 A1 Nov. 6, 2003

Related U.S. Application Data

(60) Provisional application No. 60/379,178, filed on May 8, 2002.

(30) Foreign Application Priority Data

Mar. 7, 2002 (EP) .................................. 02075971

(51) Int. Cl.
C09D 129/14 (2006.01)
C09D 201/06 (2006.01)
C09D 175/04 (2006.01)
C08K 5/37 (2006.01)

(52) U.S. Cl. .................. 525/350; 524/874; 524/355 R; 524/355 N; 524/355 EN; 106/287.23; 106/287.25; 106/287.3; 106/14.15; 106/14.42

(58) Field of Classification Search ................ 525/350; 524/874, 355 R, 355 N, 355 EN
See application file for complete search history.

(56) References Cited

U.S. PATENT DOCUMENTS

| | | | | |
|---|---|---|---|---|
| 4,448,908 A | * | 5/1984 | Pauly et al. ................. | 523/201 |
| 4,663,410 A | * | 5/1987 | Pinschmidt et al. ........ | 526/263 |
| 4,814,226 A | * | 3/1989 | Goldstein ................... | 442/327 |
| 4,990,577 A | | 2/1991 | Noomen et al. ............ | 525/454 |
| 5,177,263 A | * | 1/1993 | Leighton et al. ............ | 564/186 |
| 5,258,477 A | * | 11/1993 | Tsai et al. ................... | 526/315 |
| 5,336,807 A | * | 8/1994 | Burgoyne et al. ........... | 564/153 |
| 5,360,876 A | * | 11/1994 | Burgoyne et al. ........... | 525/374 |
| 5,521,011 A | | 5/1996 | Ishidoya et al. ............ | 428/413 |
| 5,840,823 A | | 11/1998 | Licht et al. .................. | 528/73 |

FOREIGN PATENT DOCUMENTS

| | | |
|---|---|---|
| DE | 26 42 071 | 3/1977 |
| DE | 39 27 992 A1 | 2/1991 |
| DE | 39 37 992 A1 * | 2/1991 |
| EP | 005 281 B1 | 11/1979 |
| EP | 109 006 A2 | 5/1984 |
| EP | 287 144 B2 | 10/1988 |
| EP | 448 224 B2 | 9/1991 |
| EP | 794 204 A2 | 9/1997 |
| EP | 794 204 A3 | 9/1997 |
| EP | 1 050 550 A2 * | 11/2000 |
| EP | 1 050 550 A3 | 11/2000 |
| EP | 1 062 288 B1 | 12/2000 |
| GB | 870994 | 6/1961 |
| GB | 1 551 239 | 8/1979 |
| WO | WO 93/17060 | 9/1993 |
| WO | WO 98/23691 | 6/1998 |
| WO | WO 00/64959 | 11/2000 |
| WO | WO 01/83578 A1 | 11/2001 |

OTHER PUBLICATIONS

European Search Report Application No. EP 02 07 5971 dated Aug. 29, 2002.
English language abstract abstracting DE 39 27 992 A1.
Tetrahedron Letters, "Intramolecular Pictet-Spengler reaction of N-alkoxy tryptamines I. Synthesis of (±)-Deamino-debromo-Eudistomin L.," vol. 30, No. 37, 1989, pp. 5009-5012.
Wendler, et al., "The copolymerization of styrene with the cyclic carbonate of glycidyl methacrylate," Die Angewandte Makromolekulare Chemie, 213, 1993, pp. 65-72.
March, J., Advanced Organic Chemistry, 4th edition, 1992, title pages and p. 1298.
Li Bassi, et al., "Photoinitiators for the Simultaneous Generation of Free Radicals and Acid Hardening Catalysts," Radcure '86 Proceedings, 4 pages.

* cited by examiner

*Primary Examiner*—David W. Wu
*Assistant Examiner*—Rip A. Lee
(74) *Attorney, Agent, or Firm*—John M. McGillycuddy; Michelle J. Burke; David H. Vickrey

(57) ABSTRACT

The invention relates to a coating composition comprising an acetal-functional binder and a thiol-functional cross-linker, wherein the acetal-functional binder is represented by the following formula

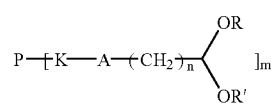

wherein P is a binder backbone, K is a divalent and/or trivalent organic moiety having 1 to 30 carbon atoms and having one or two links to the binder backbone, A is selected from oxygen, sulphur, and $NR^{VII}$, wherein $R^{VII}$ is hydrogen or an alkyl group with 1 to 4 carbon atoms, m is an integer from 1 to 50, n is an integer from 1 to 10, and R and R' may be the same or different and represent alkyl groups with 1 to 4 carbon atoms. In a further aspect, the invention relates to acetal-functional binders, acetal-functional monomers, a process for the preparation of said monomers, coating compositions comprising said acetal-functional binders, and to a process for the preparation of a coating composition comprising an acetal-functional polyurethane dispersion and a thiol-functional cross-linker.

16 Claims, No Drawings

COATING COMPOSITION COMPRISING AN ACETAL-FUNCTIONAL BINDER

This application claims the benefit of European Patent Application No. 002075971.8, filed Mar. 7, 2002, and U.S. Provisional Patent Application No. 60/379,178, filed May 8, 2002.

FIELD OF THE INVENTION

The invention relates to a coating composition comprising an acetal-functional binder and a thiol-functional cross-linker and to an adhesive composition comprising the same.

In a further aspect, the invention relates to acetal-functional binders, a coating composition comprising said acetal-functional binders, acetal-functional ethylenically unsaturated polymerizable monomers, a process for the preparation of said monomers, and to a process for the preparation of a coating composition comprising an acetal-functional polyurethane dispersion and a thiol-functional cross-linker.

The invention also relates to the use of the coating composition and to coated substrates.

BACKGROUND OF THE INVENTION

European patent publication EP-A-0 005 281 discloses a liquid coating composition based on an ester thiol and an aminoplast curing agent. The aminoplast curing agent is based on, preferably etherified, N-methylol groups, which are obtained by the reaction of amino or amido groups-containing compounds and formaldehyde. Etherified N-methylol groups can be described as N,O-acetals. The ester thiol is built up on the one hand from one or more polyhydroxyl compounds, and on the other hand from one or more mercaptocarboxylic acids.

A drawback to coating compositions based on such curing agents comprising (etherified) N-methylol groups is the possible release of formaldehyde during application and curing, and even during use of the coated object. Due to the toxicity of formaldehyde, the release of even small amounts of this compound is highly undesirable.

The coating composition of EP-A-0 005 281 is cured at elevated temperature, between 60° and 160° C. Although curing within this temperature range may be acceptable for many purposes, the need to cure in an oven at elevated temperature undesirably limits the possible application areas of the coating composition. Thus the coating composition is not suitable for the (re)finishing of cars, large transportation vehicles, and airplanes.

Water borne coating compositions are not disclosed in EP-A-0 005 281.

Polymers and binders based on aminoacetals represented by formula I

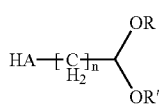

I wherein A is NH, n is an integer from 1 to 10 and R and R' may be the same or different and represent alkyl groups with 1 to 4 carbon atoms, are known in the art, for example from United States patent publication U.S. Pat. No. 4,663,410 and European patent publication EP-A 1 050 550. Aminoacetals of formula I can be used for the preparation of acetal-functional binders, which are appreciated for their capacity to be cross-linked with one another and/or other polymer or substrate-reactive groups under mild conditions to give binders, adhesives and/or coatings with good water and solvent resistance and good substrate adhesion. Cross-linking reactions of acetal-functional binders are generally acid catalyzed. Therefore, in order to prevent an equimolar amount of acidic catalyst being necessary to neutralize the basic amino group of the aminoacetal, said amino group must be transformed into a non-basic group such as an amide group, urethane group, or urea group.

In U.S. Pat. No. 4,663,410 it is proposed to prepare polymerizable amide acetals by reacting aminoacetals with, e.g., (meth)acrylic acid chloride. Drawbacks to said known process are the use of the highly toxic (meth)acryloyl chloride and the formation of an equimolar amount of chloride salt. Moreover, the high polarity of the obtained acrylamidoacetal may give problems when it is used as a (co)monomer in polymerization processes.

Also the direct reaction of an aminoacetal with either a polymerizable monoisocyanate such as m-isopropenyl-dimethylbenzyl isocyanate or with a polyisocyanate, such as described in EP-A 1 050 550, is a problematic route towards acid curable acetal-functional binders, as said reaction is attended with the formation of urea groups which generally give rise to crystalline and/or sparingly soluble materials. Crystallinity and poor solubility render the preparation of acetal-functional binders difficult and further detract from the film forming properties of a coating composition containing such acetal-functional binders. These drawbacks become more apparent as a higher proportion of acetal-functional groups is introduced into the acetal-functional binder, as it will be the case in more demanding applications which call for a high cross-link density.

SUMMARY OF THE INVENTION

It is a first object of the invention to provide a coating composition comprising an acetal-functional binder and a thiol-functional cross-linker, which composition does not release formaldehyde, is curable at a lower temperature than is known from EP-A-0 005 281, and which can be water borne or solvent borne.

In a second aspect, the invention aims at new acetal-functional binders which can be prepared without salt formation, have a lower tendency to crystallize than urea derivatives, and which are soluble in common solvents.

It is to be understood that the terms "binder" and "cross-linker" encompass polymers, oligomers, and monomers.

DETAILED DESCRIPTION OF THE INVENTION

The first object of the invention is achieved with a coating composition according to the opening paragraph, characterized in that the acetal-functional binder is represented by formula II

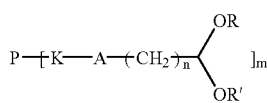

II wherein
P is a binder backbone,
A is selected from oxygen, sulphur, and $NR^{VII}$, wherein $R^{VII}$ is hydrogen or an alkyl group with 1 to 4 carbon atoms,
m is an integer from 1 to 50,
K is a divalent and/or trivalent organic moiety having 1 to 30 carbon atoms, optionally comprising hydrogen, oxygen, nitrogen and/or sulphur atoms, and having one link to the binder backbone when K is divalent and two links to the binder backbone when K is trivalent, and the individual moieties $K_1$ to $K_m$ may be the same or different,
n is an integer from 1 to 10, and
R and R' may be the same or different and represent alkyl groups with 1 to 4 carbon atoms.

In formula II m represents the number of acetal-functional groups linked to the binder backbone.

The term binder backbone is not to be understood to be restricted to the main chain of a polymer or oligomer, but is to include atoms and groups protruding therefrom.

In the case of a monomeric binder the binder backbone can also be an atom or group.

The coating composition according to the invention does not release formaldehyde, is curable at a lower temperature than is known from EP-A-0 005 281, and can be water borne or solvent borne.

If a carbonyl group is directly linked to A in formula II, K in formula II is

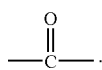

Preferably, A in formula II is $NR^{VII}$, when a carbonyl group is directly linked to A. It has further been found that acetal-functional binders according to formula II have a lower tendency to crystallize than urea derivatives, and are soluble in common solvents, when K in formula II is a divalent organic moiety comprising an —O-bond linked to the binder backbone and the individual moieties $K_1$ to $K_m$ may be the same or different and are selected from the moieties represented, by (i) the structure of formula IIIa and (ii) the structure of formula IIIb,

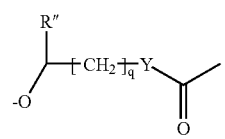

wherein q is 0, 1, 2, 3 or 4,
Y is oxygen or methylene, and
R" is hydrogen or an organic group having 1 to 30 carbon atoms, which organic group optionally may contain atoms and groups selected from oxygen, sulphur, nitrogen, hydroxyl, ester, ether, urethane, and amide.

These acetal-functional binders can be prepared without salt formation. Due to these favourable properties, such acetal-functional binders are preferred.

The preferred acetal-functional binders are suitably prepared from hydroxyl-functional intermediates obtainable by reacting aminoacetals of formula Ia

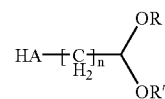

wherein A is $NR^{VII}$, n is an integer from 1 to 10, R and R' may be the same or different and represent alkyl groups with 1 to 4 carbon atoms, and $R^{VII}$ is hydrogen or an alkyl group with 1 to 4 carbon atoms,
with a cyclic ester (lactone) or a cyclic carbonate of formula IV:

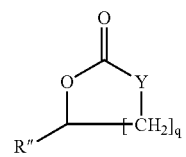

wherein q is 0, 1, 2, 3 or 4,
Y is oxygen or methylene, and
R' is hydrogen or an organic group having 1 to 30 carbon atoms, which organic group optionally may contain atoms and groups selected from oxygen, sulphur, nitrogen, hydroxyl, ester, ether, urethane, and amide.

Examples of suitable acetals Ia for this reaction are dialkyl acetals of 2-aminoacetaldehyde, 2-alkylaminoacetaldehyde, 3-aminopropionaldehyde, and 4-aminobutyraldehyde.

Examples of cyclic structures IV which can be used for the preparation of the acetal-functional intermediates include β- or γ-butyrolactone, δ- or γ-valerolactone, γ- or δ-caprolactone, ethylene carbonate, propylene carbonate, glycerol carbonate or glycerol cyclocarbonatomethacrylate.

The reaction of an aminoacetal according to formula Ia and a cyclic compound according to formula IV is suitably carried out by mixing together substantially equimolar amounts of the cyclic component and the aminoacetal in a vessel and stirring the mixture between 0° C. and 120° C. until the desired conversion is reached. If desired, a molar excess of the cyclic component according to formula IV may be employed. The reaction can be monitored by titration of the amine number. A suitable minimum amine conversion is 85%, preferred is an amine conversion of more than 90%.

If Y in formula IV is oxygen, generally, a mixture of two isomers is formed in the reaction of an aminoacetal according to formula Ia and a cyclic compound according to formula IV, represented by formulae Va and Vb,

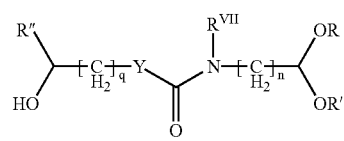

-continued

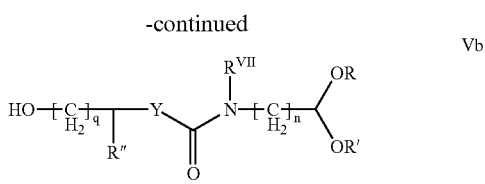

wherein n is an integer from 1 to 10, and

R and R' may be the same or different and represent alkyl groups with 1 to 4 carbon atoms, $R^{VII}$ is hydrogen or an alkyl group with 1 to 4 carbon atoms, q is 0 or an integer from 1 to 4, and R" is hydrogen or an organic group having 1 to 30 carbon atoms, which organic group optionally may contain atoms and groups selected from oxygen, sulphur, nitrogen, hydroxyl, ester, ether, urethane, and amide.

The ratio of the isomers Va and Vb can vary depending on the reaction conditions. It may also be that under special circumstances essentially one of the two possible isomers is formed.

If Y in formula IV is methylene, only the isomer represented by formula Va is formed in the reaction of the cyclic compound with an aminoacetal.

Suitable acetal-functional binders can be obtained by reacting compounds represented by formulae Va and Vb with hydroxyl-reactive functional polymers, oligomers or monomers. Examples of suitable hydroxyl-reactive functional groups are isocyanate groups, ester groups, acid chloride groups, epoxide groups, and carboxylic anhydride groups.

Such acetal-functional binders are suitable for cross-linkable compositions comprising said binder and an acetal-reactive cross-linker, such as a thiol-functional or a hydroxyl-functional cross-linker.

It has further been found that such acetal-functional binders are self-cross-linkable, i.e. cross-linking can also be effected in the absence of an additional acetal-reactive cross-linker.

According to the invention, diols Va and Vb will be obtained when in the above formulae IV, Va, and Vb R" has the meaning of a hydroxyalkyl group. The obtained diol can advantageously be used as a comonomer in the preparation of acetal-functional polyurethanes.

Acetal-functional Polyurethanes

Suitable acetal-functional binders for the coating composition according to the invention are acetal-functional polyurethanes. Acetal-functional polyurethanes can be prepared according to generally known methods by reacting a) an organic polyisocyanate, b) one or more polyalcohols containing 2 to 6 hydroxyl groups and having a number average molecular weight up to 400 and/or c) a polymeric polyol having a number average molecular weight between about 400 and about 3,000, and d) optionally compounds containing at least two isocyanate-reactive groups, such as diamines or dithiols, e) in order to achieve acetal functionality in the resulting polyurethanes, an isocyanate-reactive, acetal-functional compound, and f) optionally compounds having one isocyanate-reactive group.

The acetal-functional polyurethane can be prepared in a conventional manner by reacting a stoichiometric amount or an excess of the organic polyisocyanate with the other reactants under substantially anhydrous conditions at a temperature between about 30° C. and about 130° C. until the reaction between the isocyanate groups and the isocyanate-reactive groups is substantially complete. The reactants are generally used in proportions corresponding to a ratio of isocyanate groups to isocyanate-reactive (usually hydroxyl) groups of from about 1:1 to about 6:1, preferably about 1:1. If an excess of the organic polyisocyanate is used, an isocyanate-terminated prepolymer is prepared in a first step. In a second step, at least one isocyanate-reactive group containing compound d) can be added.

The organic polyisocyanate used in making the acetal-functional polyurethane binder can be an aliphatic, cycloaliphatic or aromatic di-, tri- or tetra-isocyanate that may be ethylenically unsaturated or not, such as 1,2-propylene diisocyanate, trimethylene diisocyanate, tetramethylene diisocyanate, 2,3-butylene diisocyanate, hexamethylene diisocyanate, octamethylene diisocyanate, 2,2,4-trimethyl hexamethylene diisocyanate, dodecamethylene diisocyanate, ω,ω'-dipropylether diisocyanate, 1,3-cyclopentane diisocyanate, 1,2-cyclohexane diisocyanate, 1,4-cyclohexane diisocyanate, isophorone diisocyanate, 4-methyl-1,3-diisocyanatocyclohexane, trans-vinylidene diisocyanate, dicyclohexyl methane-4,4'-diisocyanate (Desmodur® W), toluene diisocyanate, 1,3-bis(isocyanatomethyl)benzene, xylylene diisocyanate, α,α, α',α'-tetramethyl xylylene diisocyanate (TMXDI®), 1,5-dimethyl-2,4-bis(2-isocyanatoethyl)benzene, 1,5-dimethyl-2,4-bis(2-isocyanatoethyl)benzene, 1,3,5-triethyl-2,4-bis(isocyanatomethyl) benzene, 4,4'-diisocyanato-diphenyl, 3,3'-dichloro-4,4'-diisocyanato-diphenyl, 3,3'-diphenyl-4,4'-diisocyanato-diphenyl, 3,3'-dimethoxy-4,4'-diisocyanato-diphenyl, 4,4'-diisocyanato-diphenyl methane, 3,3'-dimethyl-4,4'-diisocyanato-diphenylmethane, diisocyanato-naphthalene, the adduct of 2 molecules of a diisocyanate, for example hexamethylene diisocyanate or isophorone diisocyanate, to a diol such as ethylene glycol, the adduct of 3 molecules of hexamethylene diisocyanate to 1 molecule of water (available under the trademark Desmodur N of Bayer), the adduct of 1 molecule of trimethylol propane to 3 molecules of toluene diisocyanate (available under the trademark Desmodur L of Bayer), the adduct of 1 molecule of trimethylol propane to 3 molecules of isophorone diisocyanate, compounds such as 1,3,5-triisocyanatobenzene and 2,4,6-triisocyanatotoluene, and the adduct of 1 molecule of pentaerythritol to 4 molecules of toluene diisocyanate. It is preferred that use be made of an aliphatic or cycloaliphatic di- or triisocyanate containing 8–36 carbon atoms.

Mixtures of polyisocyanates can be used and also polyisocyanates which have been modified by the introduction of urethane, allophanate, urea, biuret, carbodiimide, uretonimine or isocyanurate residues.

Suitable polyalcohols which can be used in the preparation of the acetal-functional polyurethane include diols and triols and mixtures thereof, but higher-functionality polyols may also be used. Examples of such lower-molecular weight polyols include ethylene glycol, diethylene glycol, tetraethylene glycol, bis(hydroxyethyl)terephthalate, cyclohexane dimethanol, furan dimethanol, glycerol, trimethylol propane, and the reaction products up to molecular weight 400 of such polyols with propylene oxide and/or ethylene oxide.

The organic polymeric polyols which can be used in the preparation of the acetal-functional polyurethane include diols and triols and mixtures thereof but higher-functionality polyols may be used, for example as minor components in admixture with diols. The polymeric polyols suitably are selected from the group of polyesters, polyester amides, polyethers, polythioethers, polycarbonates, polyacetals, polyolefins, and polysiloxanes.

Polyester polyols which can be used include hydroxyl-terminated reaction products of polyhydric alcohols, such as ethylene glycol, propylene glycol, diethylene glycol, neopentyl glycol, 1,4-butane diol, 1,6-hexane diol, furan dimethanol, dimethylol cyclohexane, glycerol, trimethylol propane or pentaerythritol or mixtures thereof with polycarboxylic acids, especially dicarboxylic acids or their ester-forming derivatives, for example succinic, glutaric, and adipic acids, or their dimethyl esters, phthalic anhydride, hexahydrophthalic anhydride or dimethyl terephthalate. Polyesters obtained by the polymerization of lactones, for example caprolactone, in conjunction with a polyol, may also be used.

Polyester amides can be obtained by the inclusion of aminoalcohols such as ethanolamine in the polyesterification mixtures.

Suitable polyether polyols include polyalkylene oxide glycol wherein alkylene oxide may be selected from ethylene oxide and/or propylene oxide units.

Polythioether polyols which can be used include products obtained by condensing thiodiglycol either alone or with other glycols, dicarboxylic acids, formaldehyde, aminoalcohols or aminocarboxylic acids.

Polycarbonate polyols include products obtained by reacting diols, such as 1,3-propane diol, 1,4-butane diol, 1,6-hexane diol, 1,4-cyclohexane dimethanol, diethylene glycol or tetraethylene glycol, with diaryl carbonates, for example diphenyl carbonate, or with phosgene.

Suitable polyolefin polyols include hydroxy-terminated butadiene homo- and copolymers.

For the introduction of acetal functionality into the polyurethane binders isocyanate reactive acetal-functional compounds are suitably used. Generally, these are compounds according to formula Ib

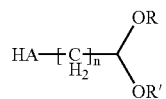

wherein A is selected from oxygen, sulphur, and $NR^{VII}$, wherein $R^{VII}$ is hydrogen or an alkyl group with 1 to 4 carbon atoms, n is an integer from 1 to 10, and R and R' may be the same or different and represent alkyl groups with 1 to 4 carbon atoms. Examples of compounds according to formula Ib are the aminoacetals mentioned above. As other specific examples 2-hydroxy-acetaldehyde dimethyl acetal and 2-mercapto-acetaldehyde dimethyl acetal may be mentioned. The preparation of the latter can be carried out as described in *Tetrahedron Letters*, 30 (37), 1989, pp. 5009–5012, or as decribed in German patent publication DE 39 279 92-A.

It is also possible to use any isocyanate-reactive derivative of aminoacetals according to formula Ia. It is preferred to use hydroxyl-functional, acetal-functional compounds according to formulae Va and Vb. It is more preferred to use acetal-functional diols which are represented by formulae Va and Vb wherein R" has the meaning of a hydroxyalkyl group. It is especially preferred to use a combination of acetal-functional mono-ols and diols according to formulae Va and Vb.

In a preferred embodiment the coating composition according to the invention comprises an acetal-functional polyurethane wherein the individual moieties $K_1$ to $K_m$ in formula II comprise di- and trivalent moieties, and $K_1$ to $K_m$ comprise —O-bonds linked to the binder backbone and are selected from the moieties represented by (i) the structure of formula IIIa, (ii) the structure of formula IIIb, (iii) the structure of formula VIa, and (iv) the structure of formula VIb

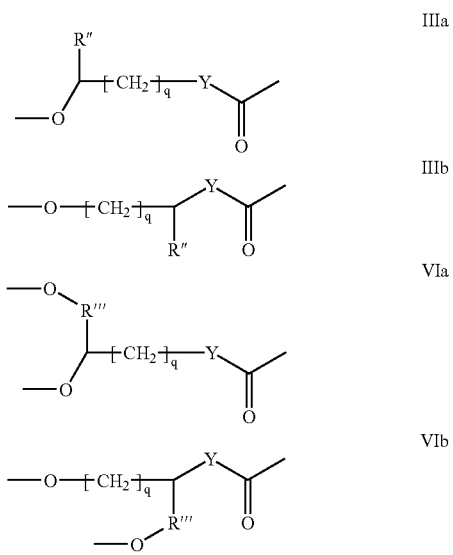

wherein q is 0 or an integer from 1 to 4,

Y is oxygen or methylene,

R" is hydrogen or an organic group having 1 to 30 carbon atoms, which organic group optionally may contain atoms and groups selected from oxygen, sulphur, nitrogen, hydroxyl, ester, ether, urethane, and amide, and R'" is an alkylene group with 1 to 30 carbon atoms.

Compounds having one isocyanate-reactive group f) may optionally be used in the preparation of the polyurethane as a chainstopper to limit the molecular weight of the polyurethane. Suitable compounds are well known in the art and include monoalcohols, monoamines, and monothiols.

The acetal-functional polyurethane binders can contain organic solvents for reduction of the viscosity. Suitable solvents are aromatic hydrocarbons such as toluene and xylene; alcohols such as ethanol, isopropanol, n-butanol, 2-butanol, hexanol, benzyl alcohol, and ketones such as methylethyl ketone, methylisobutyl ketone, methylamyl ketone, and ethylamyl ketone; esters such as butyl acetate, butyl propionate, ethoxyethyl propionate, ethylglycol acetate, butylglycol acetate, and methoxypropyl acetate; ethers such as 2-methoxypropanol, 2-methoxybutanol, ethylene glycol monobutyl ether, propylene glycol monopropyl ether, propylene glycol monobutyl ether, dioxolane or mixtures thereof. Other suitable solvents are N-methyl-2-pyrrolidone, dimethyl carbonate, propylene carbonate, butyrolactone, caprolactone, etc.

In a special embodiment, the acetal-functional polyurethane binders are present in the form of an aqueous dispersion or solution. It is then appropriate to facilitate the dispersion or dissolution of the organic polyurethane binder in water with the aid of external emulsifiers or by ionic and/or non-ionic stabilizing groups built into the polyurethane.

Suitable ionic stabilizing groups can be derived from carboxylic acid groups, sulphonic acid groups, phosphorous acid groups, phosphoric acid groups, and phosphonic acid groups.

Carboxylic acid groups can be introduced into the polyurethanes by the co-reaction of hydroxy carboxylic acids. Dimethylol propionic acid, hydroxypivalic acid, and hydroxystearic acid are preferred.

Sulphonate groups or sulphonic acid groups can be introduced into a polyurethane, for example, by co-reaction with isocyanates and with hydroxyl- or amine-functional compounds comprising at least one sulphonic acid group or sulphonate group, for example, 2-hydroxyethane sulphonic acid, the sodium salt of 2-aminoethane sulphonic acid, 3-cyclohexylamino-1-propane sulphonic acid, the reaction product of an aminoalkylsulphonic acid or its salt with an epoxide-functional compound, the reaction product of sodium 5-sulphoisophthalate with an equivalent excess of diols, triols or epoxy compounds, in which case the reaction product may contain reacted units of polycarboxylic acids such as adipic acid, phthalic acid, isophthalic acid, hexahydrophthalic anhydride, trimellitic anhydride, etc.

It is preferred that more than 50% of the sulphonic acid groups and carboxylic acid groups of the acetal-functional polyurethane binder are neutralized with a base.

Advantageously, the neutralizing agent is ammonia and/or an amine. Tertiary amines are preferred. Examples of suitable tertiary amines include trimethyl amine, triethyl amine, triisopropyl amine, triisopropanol amine, N,N-dimethyl ethanol amine, dimethyl isopropyl amine, N,N-diethyl ethanol amine, 1-dimethyl amino-2-propanol, 3-dimethyl amino-1-propanol, 2-dimethyl amino-2-methyl-1-propanol, N-methyl diethanol amine, N-ethyl diethanol amine, N-butyl diethanol amine, N-ethyl morpholine. Suitable primary amines are, for example, isopropyl amine, butyl amine, ethanolamine, 3-amino-1-propanol, 1-amino-2-propanol, 2-amino-2-methyl-1-propanol or 2-amino-2-methyl-1,3-propane diol. Secondary amines that can be used are, for example, morpholine, diethyl amine, dibutyl amine, N-methyl ethanolamine, diethanol amine, or diisopropanol amine. Alternatively, alkali metal hydroxides such as sodium hydroxide or potassium hydroxide can be used as neutralizing agents. Neutralization can be carried out prior to, during or after polyurethane formation.

The acetal-functional polyurethane binders present as an aqueous dispersion can also comprise non-ionic stabilizing groups. Non-ionic stabilizing groups can comprise $C_1$–$C_4$ alkoxy polyalkylene oxide groups. The preferred alkylene oxide groups are ethylene oxide groups, but propylene oxide groups or mixtures of ethylene oxide groups and propylene oxide groups are useful as well. For example, the alkylene oxide groups may be $C_1$–$C_4$ alkoxy ethers of polyalkylene glycols represented by formula VII:

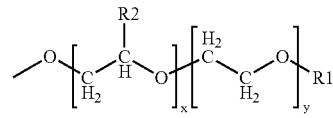

VII wherein R1 is a hydrocarbon radical with 1 to 4, preferably 1 or 2, carbon atoms; R2 is a methyl group; x is between 0 and 40, preferably between 0 and 20, most preferably between 0 and 10; y is between 0 and 50, and x+y is between 2 and 50, preferably between 2 and 25. Examples are $C_1$–$C_4$ alkoxy poly$C_2$($C_3$)alkylene oxide glycol and/or $C_1$–$C_4$ alkoxy poly$C_2$($C_3$)alkylene oxide 1,3-diol, wherein poly$C_2$($C_3$)alkylene oxide stands for polyethylene oxide, optionally comprising propylene oxide units. Suitably, the polyurethane comprises 2.5 to 15 wt. % $C_1$–$C_4$ alkoxy polyalkylene oxide groups with a number average molecular weight of 500 to 3,000, Suitable compounds comprising $C_1$–$C_4$ alkoxy polyalkylene oxide groups contain at least one isocyanate reactive group. Examples are methoxy poly$C_2$($C_3$)alkylene oxide glycols and methoxy poly$C_2$($C_3$)alkylene oxide-1,3-diols, such as Tegomer® D-3123 (PO/EO=15/85; Mn=1,180), Tegomer® D-3409 (PO/EO=0/100; Mn=2,240), and Tegomer® D-3403 (PO/EO=0/100; Mn=1,180) available from Goldschmidt AG, Germany, and MPEG 750 and MPEG 1000. Polyester polyols comprising polyalkylene oxide groups can be used as well.

The introduction of the compounds comprising $C_1$–$C_4$ alkoxy polyalkylene oxide groups and at least one isocyanate reactive group into the polyurethane can be conducted in the course of the polyurethane preparation.

A further suitable class of non-ionic stabilizing groups for water borne acetal-functional binders is formed by polyoxazolines.

In view of the acid-catalyzed cross-linking reactions of acetal-functional binders, non-ionic stabilizing groups, and sulphonate-based stabilizing groups are preferred over carboxylate stabilizing groups.

Mixing the acetal-functional polyurethane binder with an aqueous medium can be done conveniently by adding water to the polyurethane solution or, alternatively, by adding the polyurethane solution to water, under agitation of the water and the polyurethane solution. The organic solvent content of the resulting emulsion or dispersion can be reduced by distillation, optionally under reduced pressure.

Acetal-functional Polyaddition Polymers

A further suitable class of acetal-functional binders are acetal-functional polyaddition polymers. Acetal-functional polyaddition polymers can be prepared according to generally known methods by (co)polymerization of suitable ethylenically unsaturated monomers in organic solution or by aqueous emulsion (co)polymerization. The polymerization can be carried out in one or more stages.

Acetal-functional, ethylenically unsaturated monomers are suitably used to introduce acetal functionality into polyaddition polymer binders. Good results are obtained when the acetal-functional, ethylenically unsaturated monomer is prepared from an ethylenically unsaturated cyclic carbonate according to formula IV, wherein Y is oxygen and R" is —$CH_2$—O—(C=O)—C($R^{IV}$)=$CH_2$, and an aminoacetal according to formula Ia. This leads to a monomer represented by formulae VIIIa and/or VIIIb. Generally a mixture of the two isomers VIIIa and VIIIb is formed.

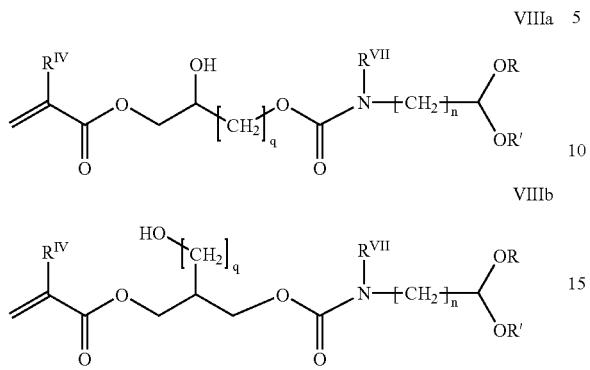

VIIIa

VIIIb wherein n is an integer from 1 to 10, q is 0 or an integer from 1 to 4,

R and R' may be the same or different and represent alkyl groups with 1 to 4 carbon atoms, $R^{IV}$ is hydrogen or methyl, and $R^{VII}$ is hydrogen or an alkyl group with 1 to 4 carbon atoms.

The reaction of the ethylenically unsaturated cyclic carbonate and an aminoacetal is carried out as described above for the reaction of cyclic compounds according to formula IV and aminoacetals according to formula Ia. If the reaction of the ethylenically unsaturated cyclic carbonate and the aminoacetal does not lead to 100% conversion, it is preferred to neutralize the residual basic nitrogen with a monoisocyanate such as m-isopropenyl-dimethylbenzyl isocyanate or 2-isocyanatoethyl methacrylate. The small amount of urea groups formed in this reaction does not distract from the solubility properties of the acetal-functional, ethylenically unsaturated monomer.

An example of an ethylenically unsaturated cyclic carbonate is glycerol cyclocarbonato methacrylate, which can be obtained from glycidol methacrylate and carbon dioxide. The formation of cyclic carbonates from epoxide compounds and carbon dioxide is described by K. Wandler, M. Fedke, S. Pabst, *Die Angewandte Makromolekulare Chemie*, 213 (1993), pp. 65–72.

In a preferred embodiment the coating composition according to the invention comprises an acetal-functional polyaddition polymer, wherein K in formula II is divalent and linked to the binder backbone via a —O-bond, and the individual moieties $K_1$ to $K_m$ may be the same or different and are selected from the moieties represented by (i) the structure of formula IXa and (ii) the structure of formula IXb,

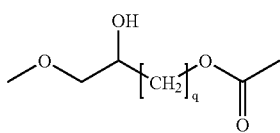

IXa

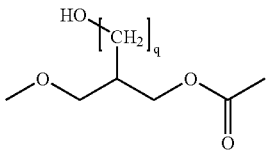

IXb wherein q is 0 or an integer from 1 to 4.

A further class of suitable acetal-functional, ethylenically unsaturated monomers is obtainable by reacting isocyanate-reactive acetal-functional compounds according to formula Ib or the hydroxyl-functional aminoacetal derivatives according to formulae Va and Vb with an ethylenically unsaturated isocyanate. The reaction between the isocyanate-reactive component and the isocyanate is carried out by stirring a substantially equimolar mixture between 0° C. and 120° C. until the isocyanate conversion reaches a minimum of 97%. The reaction is preferably carried out in the presence of a catalyst such as dibutyl tin dilaurate, tin (II) octanoate or a tertiary amine such as diazabicyclo[2.2.2]octane in a concentration between 20 and 5,000 ppm. Suitable ethylenically unsaturated isocyanates are m-isopropenyl-dimethyl benzyl isocyanate and 2-isocyanatoethyl (meth)acrylate.

In the preparation of acetal-functional, ethylenically unsaturated monomers use may be made of an inert solvent, which is preferably removed by vacuum distillation prior to the use of the obtained monomer in a subsequent emulsion polymerization process. Instead of using a solvent, use may be made of one or more reactive diluents which may serve both as comonomer and as solvent. The reactive diluents should be free of any functional groups which might interfere with the cyclocarbonate-amine and/or the isocyanate addition reaction. Suitable reactive diluents include alkyl (meth)acrylates, styrene, and other ethylenically unsaturated monomers.

Suitable other monomers to be used in the preparation of acetal-functional polyaddition polymer binders are esters of acrylic or methacrylic acid having 1 to 18 carbon atoms, preferably 1 to 12 carbon atoms, in the alcohol part, such as methyl (meth)acrylate, ethyl (meth)acrylate, propyl (meth)acrylate, isopropyl (meth)acrylate, n-butyl (meth)acrylate, isobutyl (meth)acrylate, tert.-butyl (meth)acrylate, hexyl (meth)acrylate, cyclohexyl (meth)acrylate, n-octyl (meth)acrylate, n-decyl (meth)acrylate, isodecyl (meth)acrylate, lauryl (meth)acrylate, 2-ethylhexyl (meth)acrylate, 3,5,5-trimethyl cyclohexyl (meth)acrylate, tert.-butyl cyclohexyl (meth)acrylate, isobornyl (meth)acrylate, stearyl (meth)acrylate, (meth)acrylates with ether groups such as 2-methoxy ethyl (meth)acrylate, 2-ethoxy ethyl (meth)acrylate, and 3-methoxy-propyl (meth)acrylate; others such as dimethyl aminoethyl methacrylate, glycidyl (meth)acrylate, 2-acetoacetoxyethyl methacrylate, and 3-(trimethoxysilyl)-propyl methacrylate. Further suitable monomers are esters of β-carboxyethyl acrylate and crotonic acid having 1 to 18 carbon atoms in the alcohol part, and (cyclo)alkyl esters of unsaturated dicarboxylic acids with 1 to 12 carbon atoms in the (cyclo)alkyl groups such as diethyl maleate and dibutyl fumarate, di(cyclo)alkyl itaconates, and di(cyclo)alkyl citraconates.

Other ethylenically unsaturated monomers suitable for the preparation of acetal-functional polyaddition polymers include vinyl aromatic compounds such as styrene, α-methyl styrene, o-, m-or p-methyl styrene, and tert.-butyl styrene; acrylamide, methacrylamide, acrylonitrile, N-alkoxy acrylamides, N-alkoxy methacrylamides; vinyl esters of $C_1$–$C_{18}$ monocarboxylic acids such as vinyl acetate, vinyl propionate, vinyl isobutyrate, vinyl esters of α-branched $C_5$–$C_{18}$ monocarboxylic acids, the vinyl esters of α-branched $C_9$–$C_{11}$ acids being preferred. Other suitable vinyl monomers include vinyl chloride, vinylidene chloride, vinyl pyrrolidone, and vinyl silanes such as vinyl trimethoxysilane and vinyl triethoxysilane.

The acetal-functional polyaddition polymer binders can also contain minor amounts up to about 10% of polymerized units of polyunsaturated monomers such as allyl methacrylate, ethylene glycol dimethacrylate, hexane diol diacrylate, trimethylol propane triacrylate, and the like.

Suitable initiators for the preparation of the polyaddition polymers are known in the art, such as di-tert. butyl peroxide, tert. butyl peroxy benzoate, tert. butyl peroxy-2-ethyl hexanoate, tert. butyl peroxy-3,5,5-trimethyl hexanoate, and the like, and azo initiators such as 2,2'-azo-bis(2-methylbutyronitrile) and 2,2'-azo-bis(isobutyronitrile).

The molecular weight of the polymers can be controlled by chain transfer agents such as n-octyl mercaptan, n-dodecyl mercaptan, tert. dodecyl mercaptan, mercaptoethanol, mercaptopropionic acid, or thioglycol.

Advanced polymerization techniques, such as group transfer polymerization (GTP), atom transfer radical polymerization (ATRP), and reversible addition fragmentation chain transfer (RAFT) polymerization, can also be used for the preparation of acetal-functional polyaddition polymer binders.

It is preferred that the acetal-functional polyaddition polymer binder is water borne. Such binders are suitably prepared by the generally known technique of aqueous emulsion polymerization.

By emulsion polymerization is meant here the polymerization of the monomer mixtures of ethylenically unsaturated monomers in water in the presence of a water-soluble or -insoluble initiator and 0.1–5 wt. % (calculated on the total monomer mixture(s)) of an emulsifier. The emulsion polymerization can be carried out as disclosed in European patent publication EP-A-0 287 144 or as in British patent publication GB 870 994.

Suitable emulsifiers for the emulsion polymerization are of an ionic and/or non-ionic nature. Examples of ionic emulsifiers include: potassium laurate, potassium stearate, potassium oleate, sodium decyl sulphate, sodium dodecyl sulphate, sodium dodecylbenzene sulphonic acid, sodium rosinate, and salts of organic derivatives of phosphorus-based acids. Examples of non-ionic emulsifiers include: linear and branched alkyl and alkylaryl polyethylene glycol and polypropylene glycol ethers and thioethers, alkyl phenoxypoly(ethyleneoxy)ethanols such as the adduct of 1 mole of nonyl phenol to 3–12 moles of ethylene oxide; alkyl (ethyleneoxy)ethanols with 8–18 carbon atoms in the alkyl groups, such as the adduct of 1 mole of dodecanol to 3–12 moles of ethylene oxide. Non-ionic emulsifiers can also be based on polyoxazolines. Examples of emulsifiers comprising ionic and non-ionic groups are the ammonium or sodium salt of the sulphate of alkyl phenoxypoly(ethyleneoxy)ethanols, such as the adduct of 1 mole of nonyl phenol to 3–12 moles of ethylene oxide, and the ammonium or sodium salt of the sulphate of alkyl (ethyleneoxy)ethanols with 8–18 carbon atoms in the alkyl groups, such as the adduct of 1 mole of $C_{12-14}$ alcohol to 3–12 moles of ethylene oxide.

Also, in emulsion polymerization, the conventional radical initiators may be used in the usual amounts. Examples of suitable radical initiators include water-soluble initiators, such as ammonium persulphate, sodium persulphate, potassium persulphate, and tert.-butyl hydroperoxide, and water-insoluble initiators, such as bis(2-ethylhexyl)peroxydicarbonate, di-n-butyl peroxydicarbonate, tert.-butyl perpivalate, cumene hydroperoxide, dibenzoyl peroxide, dilauroyl peroxide, 2,2'-azobisisobutyronitrile, and 2,2'-azobis-2-methylbutyronitrile. As suitable reducing agents which may be used in combination with, e.g., a hydroperoxide may be mentioned: ascorbic acid, sodium sulphoxylate formaldehyde, thiosulphates, bisulphates, hydrosulphates, water-soluble amines such as diethylene triamine, triethylene tetramine, tetraethylene pentamine, N,N-dimethyl ethanolamine, and N,N-diethyl ethanolamine, and reducing salts such as cobalt, iron, nickel, and copper sulphate.

Emulsion polymerization of the monomer mixtures generally is carried out at atmospheric pressure at a temperature of 40°–100° C., preferably 60°–90° C., in an atmosphere of an inert gas, such as nitrogen. Optionally, however, emulsion polymerization may also be carried out at elevated pressure. The reaction conditions should be chosen in such a manner, however, that other than the unsaturated bonds, functional groups present in the monomer mixtures cannot react with each other. It is preferred that measures are taken to prevent the pH of the aqueous phase from decreasing below a value of about 3 during emulsion polymerization. This can suitably be achieved by adding buffers or alkaline additives.

It is also suitable to prepare waterborne acetal-functional polyaddition polymer binders by a two-step process. In the first step the acetal-functional polyaddition polymer binder is prepared by the polymerization of suitable ethylenically unsaturated monomers as described above in an essentially non-aqueous environment, optionally in the presence of an organic solvent. In the second step of said two-step process mixing the acetal-functional polyaddition polymer binder with an aqueous medium can be done conveniently by adding water to the polyaddition polymer or, alternatively, by adding the polyaddition polymer to water, under agitation. The organic solvent content of the resulting emulsion or dispersion can be reduced by distillation, optionally under reduced pressure Other Acetal-functional Binders Acetal-functional binders obtainable by amidation of esters with acetal-functional compounds according to formula Ia wherein A is $NR^{VII}$ can also be used in the coating composition of the invention. The preparation of suitable acetal-functional binders of this kind is for example described in United States patent U.S. Pat. No. 5,360,876.

It has been found that acetal-functional malonamides of formula X,

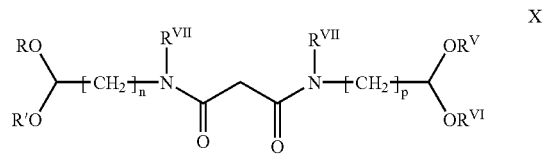

wherein
n and p may be the same or different and represent integers from 1 to 10,
R, R', $R^V$ and $R^{VI}$ may be the same or different and represent alkyl groups with 1 to 4 carbon atoms, and $R^{VII}$ is hydrogen or an alkyl group with 1 to 4 carbon atoms, can advantageously be used as acetal-functional binders in the coating composition of the invention. The aminoacetal derivatives according to formula X can be obtained by amidation of malonic acid esters with aminoacetals of formula Ia. It is preferred that malonic acid esters of lower alcohols are used, such as dimethyl, diethyl or dipropyl malonate. The amidation is suitably carried out by contacting the malonic acid ester and the aminoacetal at elevated temperature, for example between about 50° and 160° C., with simultaneous distillative removal of the alcohol formed.

It has further been found that the malonamide according to formula X, wherein n and p are 3, R, R', $R^V$, and $R^{VI}$ are ethyl, and $R^{VII}$ is hydrogen, is a liquid, whereas polyfunctional acetal-functional amides generally are solids, as disclosed in U.S. Pat. No. 5,360,876. Liquid acetal-functional amides are pre-eminently suitable for use as acetal-functional binders or reactive diluents in high solids coating compositions as well as in water borne coating compositions according to the invention.

Another useful class of acetal-functional binders for the coating composition of the invention is formed by acetal-functional alkyd resins, which are obtainable by reaction of ester-or isocyanate-functional alkyd resins with aminoacetals according to formula Ia, wherein A is $NR^{VII}$. The preparation of such acetal-functional alkyd resins is described in European patent publication EP-A-1 062 288. It is also possible to use a preparation process for acetal-functional binders analogous to the process disclosed in EP-A-1 062 288, in which instead of the aminoacetals of formula I acetal derivatives according to formulae Va and Vb are employed.

A further class of acetal-functional binders useful in the coating composition according to the current invention can be obtained by the base catalyzed nucleophilic addition of acetals according to formula Ib, wherein A is sulphur or oxygen, to electron-depleted ethylenically unsaturated groups. Suitable compounds with electron-depleted ethylenically unsaturated groups include any compound containing two or more ethylenically unsaturated groups, with the ethylenically unsaturated groups comprising at least one electron-withdrawing functionality linked to a carbon atom of the unsaturated bond, as described in WO 00/64959 incorporated herein by reference.

The electron-depleted ethylenically unsaturated groups can also be covalently attached to a resin. Suitable resins of this type include (meth)acryloyl-functional polyaddition polymers, polyurethanes, and polyesters. Examples of such resins are described in U.S. Pat. No. 4,990,577 and references cited therein.

A still further class of acetal-functional binders is obtainable by reaction of alkoxy silane-functional precursors with acetals according to formula Ib, wherein A is oxygen. Suitable compounds with alkoxy silane groups are well known in the art. Examples are described in WO 98/23691.

The Thiol-functional Cross-linker

Suitable thiol-functional cross-linkers can be prepared by esterification of hydroxyl group-containing compounds with thiol group-containing acids, such as 3-mercapto propionic acid, 2-mercapto propionic acid, thio-salicylic acid, mercapto succinic acid, mercapto acetic acid, or cysteine. Examples of suitable hydroxyl group-containing compounds are diols, triols, and tetraols, such as 1,4-butane diol, 1,6-hexane diol, 2,2-dimethyl-1,3-propane diol, 2-ethyl-2-propyl-1,3-propane diol, 1,2-, 1,3-, and 1,4-cyclohexane diols, and the corresponding cyclohexane dimethanol, 1,1,1-trimethylol propane, 1,2,3-trimethylol propane, and pentaerythritol. Examples of compounds prepared according to such a method include pentaerythritol tetrakis (3-mercapto propionate), pentaerythritol tetrakis (2-mercapto acetate), trimethylol propane tris (3-mercapto propionate), trimethylol propane tris (2-mercapto propionate), and trimethylol propane tris (2-mercapto acetate). Good results have been obtained with trimethylol propane tris (3-mercapto propionate) and pentaerythritol tetrakis (3-mercapto propionate).

A further example of a compound prepared according to such a method consists of a hyperbranched polyol core based on a starter polyol, e.g., trimethylol propane, and dimethylol propionic acid. This polyol is subsequently esterified with 3-mercapto propionic acid and isononanoic acid. These methods are described in European patent application EP-A 0 448 224 and International patent application WO 93/17060.

The thiol-functional cross-linker can also be a compound generally obtainable by reacting epoxide-functional compounds with hydrogen sulphide. Such thiol-functional cross-linkers also comprise hydroxyl groups. An example of such a thiol-functional cross-linker may have the following formula:

$T-[(O-CHR-CH_2-O)_n CH_2CH(XH)CH_2YH]_m$, with T being an m valent organic moiety, R being hydrogen or methyl, n being an integer between 0 and 10, X and Y being oxygen or sulphur, with the proviso that X and Y are not equal. An example of such a compound is commercially available from Cognis under the trademark Capcuree® 3/800.

Other syntheses to prepare thiol-functional cross-linkers involve: the reaction of an aryl or alkyl halide with NaHS to introduce pendant mercapto groups into the alkyl and aryl compounds, respectively; the reaction of a Grignard reagent with sulphur to introduce pendant mercapto groups into the structure; the reaction of a polymercaptan or $H_2S$ with a polyolefin according to a nucleophilic reaction, an electrophilic reaction or a radical reaction; the reaction of disulphides; and other routes such as mentioned in Jerry March, *Advanced Organic Chemistry*, $4^{th}$ edition, 1992, page 1298.

The thiol-functional cross-linker can be a resin having as a backbone a polyester resin, a polyurethane resin, a polyacrylate resin, or a polyether resin.

The thiol-functional cross-linker can be a polyester prepared from (a) at least one polycarboxylic acid or reactive derivatives thereof, (b) at least one polyol, and (c) at least one thiol-functional carboxylic acid. The polyesters preferably possess a branched structure. Branched polyesters are conventionally obtained through condensation of polycarboxylic acids or reactive derivatives thereof, such as the corresponding anhydrides or lower alkyl esters, with polyalcohols, when at least one of the reactants has a functionality of at least 3.

Examples of suitable polycarboxylic acids or reactive derivatives thereof are tetrahydrophthalic acid, tetrahydrophthalic anhydride, hexahydrophthalic acid, hexahydrophthalic anhydride, methyl hexahydrophthalic acid, methyl hexahydrophthalic anhydride, dimethyl cyclohexane dicarboxylate, 1,4-cyclohexane dicarboxylic acid, 1,3-cyclohexane dicarboxylic acid, phthalic acid, phthalic anhydride, isophthalic acid, terephthalic acid, 5-tert. butyl isophthalic acid, trimellitic anhydride, maleic acid, maleic anhydride, fumaric acid, succinic acid, succinic anhydride, dodecenyl succinic anhydride, dimethyl succinate, glutaric acid, adipic acid, dimethyl adipate, azelaic acid, and mixtures thereof.

Examples of suitable polyols include trimethylol propane, trimethylol ethane, glycerol, 1,2,6-hexanetriol, ethylene glycol, 1,2-propylene glycol, 1,3-propylene glycol, 2-methyl-propane-1,3-diol, neopentyl glycol, 2-butyl-2-ethyl-1,3-propane diol, cyclohexane-1,4-dimethylol, the monoester of neopentyl glycol and hydroxypivalic acid, hydrogenated Bisphenol A, 1,5-pentane diol, 3-methyl-pentane diol, 1,6-hexane diol, 2,2,4-trimethyl pentane-1,3-diol, dimethylol propionic acid, pentaerythritol, di-trimethylol propane, dipentaerythritol, and mixtures thereof.

Examples of suitable thiol-functional organic acids include 3-mercaptopropionic acid, 2-mercaptopropionic acid, thio-salicylic acid, mercaptosuccinic acid, mercaptoacetic acid, cysteine, and mixtures thereof.

Optionally, monocarboxylic acids and monoalcohols may be used in the preparation of the polyesters. Preferably, $C_4-C_{18}$ monocarboxylic acids and $C_6-C_{18}$ monoalcohols are used. Examples of the $C_4-C_{18}$ monocarboxylic acids include pivalic acid, hexanoic acid, heptanoic acid, octanoic acid, nonanoic acid, 2-ethylhexanoic acid, isononanoic acid, decanoic acid, lauric acid, myristic acid, palmitic acid, isostearic acid, stearic acid, hydroxystearic acid, benzoic acid, 4-tert. butyl benzoic acid, and mixtures thereof. Examples of the $C_6-C_{18}$ monoalcohols include cyclohexanol, 2-ethylhexanol, stearyl alcohol, and 4-tert. butyl cyclohexanol.

The thiol-functional cross-linker can be a thiol-functional polyacrylate. Such a polyacrylate is derived from hydroxyl-functional acrylic monomers, such as hydroxy ethyl (meth)acrylate, hydroxy propyl (meth)acrylate, hydroxy butyl (meth)acrylate, other acrylic monomers such as (meth)acrylic acid, methyl (meth)acrylate, butyl (meth)acrylate, optionally in combination with a vinyl derivative such as styrene, and the like, or mixtures thereof, the terms (meth)acrylate and (meth)acrylic acid referring to both methacrylate and acrylate, as well as to methacrylic acid and acrylic acid, respectively. The thiol group is introduced by esterification of (part of) the hydroxyl groups of the acrylate copolymer with one or more of the thiol-functional carboxylic acids described above.

Alternatively, glycidyl methacrylate is introduced into the polymer to prepare an epoxy-functional polyacrylate. The epoxy groups are then reacted with suitable thiol-functional carboxylic acids such as mentioned above. Alternatively, the thiol group can be introduced by reacting an isocyanate-functional polyacrylate with a thiol-functional alcohol, e.g., mercapto ethanol. The polyacrylate is prepared by conventional methods, for instance, by the slow addition of appropriate monomers to a solution of an appropriate polymerization initiator, such as an azo or peroxy initiator.

Also included in the coating composition of the invention can be mono-, di-, tri-, or higher thiol-functional compounds such as ethane dithiol or bis-beta-mercapto-ethyl sulphide, thiophenol, 2-mercaptoethanol, 1,4-butane dithiol, 2,3-dimercapto propanol, dodecane dithiol, 1,6-hexane dithiol, 1-octane thiol, dodecyl thiol, cyclohexyl mercaptan, and the like, and mixtures thereof.

Good results were obtained when for the thiol-functional cross-linker use was made of an aqueous mercaptan-functional polyurethane dispersion. The preparation of thiol-functional polyurethane dispersions is known and described in German patent publication DE-A-26 42 071 and European patent publication EP-A-0 794 204. Thus far optimum results have been obtained with an aqueous mercaptan-functional polyurethane dispersion which is obtainable by first preparing an isocyanate-functional polyurethane from diols, diisocyanates, and building blocks containing groups which facilitate the stabilization of the resin in an aqueous dispersion, followed by reaction of the isocyanate-functional polyurethane with a polyfunctional thiol in a base-catalyzed addition reaction, and dispersion of the obtained reaction product in water.

It is well known in the art that the average functionality of a cross-linker is at least two. It is to be understood that this applies also to the thiol-functional cross-linker used in the current invention.

The molar ratio of acetal-functional groups to thiol groups in the coating composition can vary within a wide range and generally is between 1.0:0.1 and 1.0:3.5., preferably between 1.0:0.1 and 1.0:2.5. A particularly preferred range is between 1.0:0.5 and 1.0:2.2. It should be realized that by an acetal-functional group a moiety is meant having a carbon atom to which two alkoxy groups are linked.

It is also within the scope of the invention that the acetal-functional groups and the thiol groups are attached to the same polymer or oligomer backbone. In this case, the acetal-functional binder and the thiol-functional cross-linker are combined in one molecule.

Other Components

The coating composition can contain acid-based catalysts, such as Brønsted and Lewis acids. Examples of suitable Lewis acids are $AlCl_3$, $SbCl_5$, $BF_3$, $BCl_3$, $BeCl_2$, $FeCl_3$, $FeBr_3$, $SnCl_4$, $TiCl_4$, $ZnCl_2$ and $ZrCl_4$ and organic complexes thereof, e.g., $BF_3Et_2O$, $BF_3-2CH_3COOH$, $BF_3-2H_2O$, $BF_3-H_3PO_4$, $BF_3-(CH_3)_2O$, $BF_3-THF$, $BF_3-2CH_3OH$, $BF_3-2C_2H_5OH$, and $BF_3-C_6H_5CH_2$,. Preferably, use is made of Brønsted acids, such as a mono-or dialkyl phosphate, a carboxylic acid having at least one chlorine and/or fluorine atom, an alkyl or aryl sulphonic acid or an (alkyl)phosphoric acid, more particularly methane sulphonic acid, paratoluene sulphonic acid, optionally substituted naphthalene sulphonic acids, dodecyl benzene sulphonic acid, dibutyl phosphate, trichloroacetic acid, phosphoric acid, and mixtures thereof. The acid catalyst can also be selected from mineral acids, e.g., hydrogen chloride. The acid catalyst may be blocked, if so desired, resulting in the release of the Lewis or Brønsted acid under the influence of, e.g., electromagnetic irradiation (visible light or UV), heat or moisture. Acid generating photoinitiators are described, int. al., in G. Li Bassi et al., "Photoinitiators for the Simultaneous Generation of Free Radicals and Acid Hardening Catalysts," Radcure '86 Proceedings, e.g., 2-methyl-1-[4-(methylthio)phenyl]-2-[4-methylphenylsulphonyl] propan-1-one (MDTA), ex Fratelli Lamberti Spa, Varese, Italy. Alternatively, use may be made of Lewis acid generating compounds such as Irgacure® 261 ex Ciba Geigy and trimethyl silyl benzene sulphonic ester.

The amount of acid catalyst generally is about 0.5 to 5 wt. % of the total binder. The pot life at ambient temperature usually is between 0.5 and 24 hours, depending on the type of polyfunctional acetal-reactive compound, the presence of catalysts, and the amount thereof.

The coating compositions can further comprise other ingredients, additives or auxiliaries, such as other polymers or polymer dispersions, pigments, dyes, emulsifiers (surfactants), pigment dispersion aids, levelling agents, anti-cratering agents, antifoaming agents, antisagging agents, heat stabilizers, UV absorbers, antioxidants, and fillers. If the coating composition comprises an acid catalyst, as mentioned above, the other ingredients, additives, and auxiliaries are preferably selected from materials having a low content of basic groups or having no basic groups. Such a selection will prevent undesirable neutralization of the acid catalyst.

This aspect is of particular importance for the selection of pigments for pigmented coatings.

Suitable types of other polymer dispersions present in the coating composition according to the invention include acrylic polymer emulsions and aqueous polyurethane dispersions.

Also included can be reactive diluents such as water-soluble mono or (preferably) polyhydric thiols, examples of which include low-molecular weight di- and trithiols such as 1,2-ethane dithiol, 1,4-butane dithiol, 1,6-hexane dithiol, and the like, and high-molecular weight polythiols such as poly(ethylene thiol), poly(p-styrene thiol), and poly(4-mercaptomethyl styrene).

The coating composition of the invention may optionally comprise additional functional groups, which can undergo supplementary cross-linking reactions. The additional functional groups can be attached to the binder, the cross-linker and/or other components present in the coating composition. Suitable additional functional groups present in the coating composition are in particular other thiol-reactive functional groups, examples of which are ethylenically unsaturated groups and epoxide groups, and other acetal-reactive functional groups, examples of which are hydroxyl groups. The coating composition can also comprise oxidatively drying groups.

It is preferred that solvent borne coating compositions according to the invention contain at most 250 g/l of organic solvent. Liquid coating compositions containing at most 10 weight-% of added organic solvent are particularly preferred. It is also within the scope of the invention to prepare liquid coating compositions which contain no added solvent.

If the coating composition is water borne, the major part of the volatile content of the coating composition of the present invention consists of water. However, about 25 wt. % of the volatile content of the composition can be an organic solvent. As suitable organic solvents may be mentioned dimethyl dipropylene glycol, methyl ether of diacetone alcohol, ethyl acetate, butyl acetate, ethyl glycol acetate, butyl glycol acetate, 1-methoxy-2-propyl acetate, butyl propionate, ethoxy ethyl propionate, toluene, xylene; methylethyl ketone, methyl isobutyl ketone, methyl amyl ketone, ethyl amyl ketone, dioxolane, N-methyl-2-pyrrolidone, dimethyl carbonate, propylene carbonate, ethylene glycol monobutylether, butyrolactone, caprolactone, and mixtures thereof.

The coating composition according to the invention can be part of a multi-component system, for instance a two-component system. For example, one component can comprise both the acetal-functional binder and the thiol-functional cross-linker. The second component can comprise an acid-based catalyst as described above.

Alternatively, a three-component system can be employed. For example, one component can comprise the acetal-functional binder. A second component can comprise the thiol-functional cross-linker. A third component can comprise an acid-based catalyst.

For aqueous acetal-functional polyurethane dispersions it has been found that the process of preparation of the coating composition influences the overall properties of the cured coating. Thus, acceptable results can be obtained when the thiol-functional cross-linker is added to the acetal-functional polyurethane dispersion with stirring. However, improved results, in particular with respect to solvent resistance and hardness of the cured coating, can be achieved if the order of addition is reversed. Accordingly, a preferred process for preparation of a coating composition according to the invention comprising an acetal-functional polyurethane dispersion comprises adding, with stirring, an acetal-functional polyurethane dispersion to a thiol-functional cross-linker which cross-linker may optionally be diluted with an organic solvent. Optimum results were obtained with a process for the preparation of a coating composition comprising an acetal-functional polyurethane dispersion and a thiol-functional cross-linker, comprising the steps of a) mixing an acetal-functional polyurethane binder and a thiol-functional cross-linker in a substantially non-aqueous medium, and b) forming an aqueous dispersion of the mixture. The formation of the aqueous dispersion can suitably be carried out as described above for the preparation of an acetal-functional polyurethane binder dispersion.

The coating composition of the present invention can be applied to any substrate. The substrate can be, for example, metal, plastic, wood, glass, ceramic, or some other coating layer. The other coating layer may be comprised of the coating composition of the current invention or it may be a different coating composition. The coating composition of the current invention can be employed as clear coat, base coat, and as pigmented top coat. The coating composition shows particular utility as primer and/or filler. The coating composition can be applied by conventional means such as by spray gun, brush, or roller, spraying being preferred. Curing temperatures preferably are between 0° and 80° C. and more preferably between 20° and 70° C. The composition is suitable for coating objects such as bridges, pipelines, industrial plants or buildings, oil and gas installations, or ships. The composition is particularly suitable in the preparation of coated metal substrates, such as in the refinish industry, in particular the body shop, to repair automobiles and transportation vehicles, and in finishing large transportation vehicles such as trains, trucks, buses, and airplanes.

The coating composition as described above can also advantageously be used as an adhesive composition. The invention will be illustrated with reference to the following examples.

EXAMPLES

The following general methods were employed, except where explicitly stated otherwise:

The dispersions' respective average particle size was determined with the aid of dynamic light scattering, with the dispersions diluted to a solids content of about 0.1 wt. %.

The solids content was determined in accordance with ASTM method No. 1644-59, with heating to 140° C. over a period of 30 minutes.

The weight average molecular weight Mw and the number average molecular weight Mn were determined using gel permeation chromatography with polystyrene as the standard.

The Persoz Hardness of the obtained coating layers was determined after 1 and 7 days of aging in accordance with French industrial standard method NF T30-016, the result being expressed in seconds.

The resistance to methylethyl ketone (MEK) and water was determined after 1 and 7 days of aging and exposure for one minute (MEK) or for one hour (water). In the resistance test 0 stands for dissolved, 3 for slightly affected, and 5 for excellent.

For testing of adhesion a cross-cut at 45° angle was made in a through-hardened coating with a disposable blade cutter. A standard type adhesion tape was stuck onto the paint and gently pulled off again. The adhesion of the paint was judged visually and was scored on a 1–10 scale (1: very bad adhesion, 10: excellent adhesion).

The appearance was judged visually. A good appearance means: a smooth surface with a high gloss. A bad appearance means: a dull, low gloss level.

Intermediate A: Preparation of a Hydroxyl-functional Acetal Intermediate According to Formula Va from γ-butyrolactone and 2-aminoacetaldehyde dimethyl acetal In a flask equipped with a magnetic stirrer, a nitrogen inlet and outlet, a reflux condenser, a thermocouple, and a heating mantle were placed γ-butyrolactone (22.5 g, 0.26 mol) and aminoacetaldehyde dimethyl acetal (27.49 g, 0.26 mol). The mixture was heated to 80° C. and stirred at this temperature for 12 h. After this time the amine number was determined as 13.7 mg KOH/g, which corresponds to a conversion of 95%. The reaction product corresponds to the the following formula.

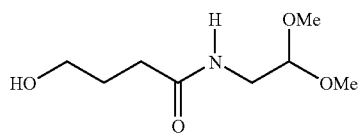

The flask was cooled to room temperature and a clear liquid was obtained.

Intermediate B: Preparation of a Hydroxyl-functional Acetal Intermediate from Propylene Carbonate and 4-aminobutyraldehyde diethyl acetal According to Formulae Va and Vb In a flask equipped with a magnetic stirrer, a nitrogen inlet and outlet, a reflux condenser, an addition funnel, a thermocouple, and a heating mantle was placed propylene carbonate (116.2 g, 1.14 mol). Aminobutyraldehyde diethyl acetal (183.8 g, 1.14 mol) was added over 1 hour, during which time the reaction mixture exothermed to 30° C. The mixture was subsequently heated to 80° C. and stirred at this temperature for 12 h. After this time the amine number was determined as 11.3 mg KOH/g, which corresponds to a conversion of 95%.

The reaction product corresponds to the the following formulae.

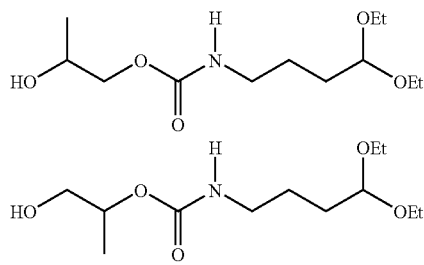

The flask was cooled to room temperature and a clear liquid was obtained.

Intermediate C: Preparation of a Hydroxyl-functional Acetal Intermediate from Glycerol Carbonate and 4-aminobutyraldehyde diethyl acetal According to Formulae Va and Vb The same procedure was followed as for intermediate B. From 118.0 g glycerol carbonate and 161.2 g aminobutyraldehyde diethyl acetal a liquid addition product was obtained. The amine number of the product was 11.3 mg KOH/g, which corresponds to a conversion of 94%. The reaction product corresponds to the the following formulae.

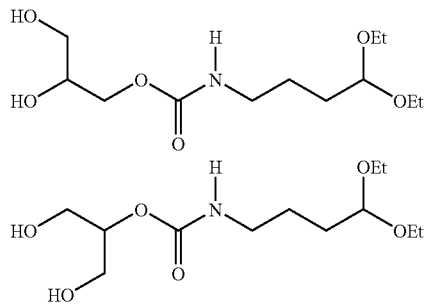

Intermediate D: Preparation of a Hydroxyl-functional Acetal Intermediate from Propylene Carbonate and 4-aminobutyraldehyde dimethylacetal According to Formulae Va and Vb The same procedure was followed as for intermediate B. From 116.2 g (1.14 mol) propylene carbonate and 151.8 g (1.14 mol) aminobutyraldehyde dimethyl acetal a liquid addition product was obtained. The amine number of the product was 10.1 mg KOH/g, which corresponds to a conversion of 95.8%.

Intermediate E: Preparation of a Hydroxyl-functional Acetal Intermediate from Glycerol Carbonate and 4-aminobutyraldehyde dimethyl acetal According to Formulae Va and Vb The same procedure was followed as for intermediate B. From 100.1 g glycerol carbonate and 112.8 g aminobutyraldehyde dimethyl acetal a liquid addition product was obtained. The amine number of the product was 8.2 mg KOH/g, which corresponds to a conversion of 96.3%.

Preparation of a Polyester Diol 1

A 2-litre 4-neck flask was fitted with a variable speed stirrer, thermocouples in combination with a controller, a distillation column, a condenser, a nitrogen sparge, and a heating mantle. In the flask were placed 836.0 g hexahydrophthalic anhydride, 962.5 g 1,6-hexane diol, and 0.45 g dibutyl tin oxide. With stirring and under nitrogen flow the mixture was heated to 250° C. and kept at this temperature for 4 hours with water being distilled off. Then the mixture was allowed to cool to room temperature. A clear, colourless polyester was obtained with an acid number of 1.6 mg KOH/g, a hydroxyl number of 179 mg KOH/g, GPC data Mn 990, Mw 1,600.

Preparation of a Polyester Diol 2

A 2-litre 4-neck flask was fitted with a variable speed stirrer, thermocouples in combination with a controller, a distillation column, a condenser, a nitrogen sparge, and a heating mantle. In the flask were placed 474.7 g hexahydrophthalic anhydride, 363.9 g 1,6-hexane diol, 160.4 g neopentyl glycol, and 0.45 g dibutyl tin oxide. With stirring and under nitrogen flow the mixture was heated to 250° C. and kept at this temperature for 4 hours with water being distilled off. Then the mixture was allowed to cool to room temperature. A clear, colourless polyester was obtained with an acid number of 1.5 mg KOH/g and a hydroxyl number of 183 mg KOH/g.

Preparation of a Hydrophilic Polyester Diol 3

A 3-litre 4-neck flask was fitted with a variable speed stirrer, thermocouples in combination with a controller, a distillation column, a condenser, a nitrogen sparge, and a heating mantle. In the flask were placed 332 g hexahydrophthalic anhydride and 1,614 g polyethylene glycol monomethyl ether of average molecular weight 750. The mixture was heated to 170° C. for 30 minutes, cooled to 140° C., and 269 g di(trimethylol propane) were added, followed by 132 g xylene and 3.3 g of an 85% aqueous phosphoric acid solution. The mixture was heated to 235° C. and water was azeotropically distilled off until the acid value of the reaction mixture was below 5 mg KOH/g. The mixture was then cooled to 180° C. and xylene was distilled off at reduced pressure. The resulting polyester diol solidified at room temperature and had an acid value of 3.9 mg KOH/g and a hydroxyl value of 59 mg KOH/g.

Preparation of Acetal-functional Polyurethane Binder Dispersion 1

A 4-neck flask was fitted with a variable speed stirrer, thermocouples in combination with a controller, a condenser, a nitrogen inlet and outlet, and a heating mantle. In the flask were placed 14.3 g of polyester diol 1 described above, 75.0 g dry 2-butanone, 29.5 g Tegomer D3403 (available from Tego Chemie Service), 59.1 g isophorone diisocyanate, 53.2 g of acetal-functional intermediate C described above, and 18.9 g of acetal-functional intermediate B described above. The mixture was stirred until homogeneous and then 0.20 g tin(II)octanoate was added. The reaction exothermed and was further heated to 80° C. and kept at this temperature for 6 hours. After this time, the isocyanate content of the mixture was below 0.1%. The mixture was cooled to 45° C. The stirrer was set to the highest speed and 430 g water were added at a rate of 10 ml/min. When the addition of water was complete, a distillation head and a vacuum pump were connected to the flask, and the pressure was gradually lowered until all 2-butanon was distilled off.

A white emulsion with the following characteristics was obtained: Solids content 32%, Mn 3,180, Mw 8,570, viscosity 280 mPas, particle size 180 nm.

Preparation of Acetal-functional Polyurethane Binder Dispersion 2

A 4-neck flask was fitted with a variable speed stirrer, thermocouples in combination with a controller, a condenser, a nitrogen in- and outlet, an addition funnel, and a heating mantle. In the flask were placed 77.03 g isophorone diisocyanate and 70 g dry 2-butanone. A mixture of 36.8 g Tegomer D3403 (available from Tego Chemie Service), 80.22 g dry 2-butanone, 23.82 g of Rucoflex S-107-210 (a polyesterdiol resulting from the reaction of adipic acid and neopentyl glycol, available from Ruco Polymers), 59.9 g of acetal-functional intermediate E, described above, 0.22 g tin(II)octanoate, and 21.14 g of acetal functional intermediate D, described above, was added during 1 hour. The mixture was further heated to 85° C. and kept at this temperature for 19 hours. After this time, the isocyanate content of the mixture was below 0.1%. The mixture was cooled to 45° C. and transferred to a 2 l round-bottom flask with baffles and the above-mentioned equipment. The stirring speed was set to 350 RPM and 435 g water were added at a rate of 2.7 ml/min. When the addition of water was complete, the emulsion was transferred to a 2 l flask fifted with the above-mentioned equipment and a distillation head. The temperature was maintained at 45° C. A vacuum pump was connected to the flask and the pressure was gradually lowered until substantially all 2-butanone was distilled off.

A transparent yellow emulsion with the following characteristics was obtained: Solids content 35.8%, Mn 3,010, Mw 6,900, viscosity (25 ° C., 1,000 RPM) 24 mPas, particle size 65 nm.

Preparation of an Acetal-functional Polyurethane Binder Dispersion Comprising a Thiol-functional Cross-linker (Acetal-functional Polyurethane Binder Dispersion 3)

The preparation of acetal-functional polyurethane binder 2 was repeated as described above until the isocyanate content of the reaction mixture was below 0.1%. 130.26 g of the resulting acetal-functional binder solution were transferred to a 500 ml round-bottom dispersion flask with baffles equipped as described above. Then 14.66 g pentaerythritol tetrakis (3-mercapto propionate) were added. The molar ratio of acetal-functional groups to thiol-functional groups was 1:2. The mixture was stirred until homogeneous and the temperature was raised to 45° C. The stirring speed was set to 350 RPM and 100 g water were added at a rate of 1.3 ml/min. When the addition of water was complete, removal of 2-butanone by distillation was carried out as above.

A white emulsion with the following characteristics was obtained: Solids content 35.4%, viscosity (25° C., 1,000 RPM) 16 mPas, particle size 124 nm.

Preparation of a Polymerizable Monomer 1 from Aminobutyraldehyde Dimethyl Acetal and meta-isopropenyl-dimethylbenzyl isocyanate (Comparative Example)

In a flask equipped with a magnetic stirrer, a $CaCl_2$ drying tube, a reflux condenser, and a dropping funnel were placed 120 g dry tetrahydrofuran and 13.3 g aminobutyraldehyde dimethyl acetal. At room temperature 21.1 g meta-isopropenyl-dimethylbenzyl isocyanate were added over 30 minutes. The reaction mixture exothermed to 35° C. during the addition period. After cooling to room temperature, the addition product of the formula

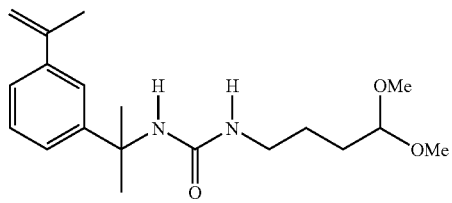

precipitated as a white solid which was virtually insoluble in tetrahydrofuran, butyl acetate, butyl acrylate, styrene or water.

Preparation of a Polymerizable Monomer 2 from Intermediate A and meta-isopropenyl-dimethylbenzyl isocyanate In a flask equipped with a magnetic stirrer, a $CaCl_2$ drying tube, a reflux condenser, and a dropping funnel were placed butyl acrylate (120 g) and intermediate A (20.0 g, 0.10 mol) and 1 drop of dibutyl tin dilaurate. At room temperature meta-isopropenyl-dimethylbenzyl isocyanate (21.1 g, 0.10 mol) was added over 30 minutes. The reaction mixture was stirred at room temperature for 16 h, after which time infrared analysis indicated the absence of the isocyanate signal at 2,270 $cm^{-1}$. The reaction product was a clear liquid.

Preparation of a Polymerizable Monomer 3 According to Formulae VIIIa and VIIIb from glycerol cyclocarbonato methacrylate and aminobutyraldehyde dimethyl acetal In a flask equipped with a magnetic stirrer, a $CaCl_2$ drying tube, a reflux condenser, and a dropping funnel and a water bath were placed ethyl acetate (300 g) and glycerol cyclocarbonate methacrylate (279.0 g, 1.50 mol). The mixture was stirred at room temperature and for 30 minutes aminobutyraldehyde dimethyl acetal (199.5 g, 1.50 mol) was added. During the addition period the reaction mixture exothermed to 55° C. At the end of the addition period, the mixture was heated to 80° C. and stirred at this temperature for 6 hours. After this time the amine number was determined to be 14.3 mg KOH/g.

Then meta-isopropenyl-dimethylbenzyl isocyanate (35.7 g, 0.23 mol) and 0.24 g hydroquinone monomethyl ether were added and the mixture was allowed to stand at room temperature for 12 h. The amine number was determined to be below 1.0 mg KOH/g. Ethyl acetate was distilled off at reduced pressure, the maximum temperature during distillation was kept below 60° C. The residue was a light yellow viscous oil, yield 514 g.

Preparation of Seed Copolymer

In a flask equipped with a mechanical stirrer, a nitrogen inlet and outlet, an addition funnel, a thermocouple, a heating mantle, and a reflux condenser were placed 1,170.0 g water, 10.0 g Triton X-165 (a non-ionic emulsifier available from Union Carbide), and 2.0 g sodium dodecyl sulphate. The mixture was heated to 80° C. Then a monomer mixture of 14.0 g butyl acrylate, 43.8 g butyl methacrylate, and 0.6 g methacrylic acid was added to the reaction flask in one go. Ten minutes after the monomer addition, a solution of 0.64 g of ammonium persulphate in 65 g of water was added to the flask in one go. The reaction was kept at 80° C. for one hour, after which time a second portion of initiator solution (0.3 g ammonium persulphate in 2.0 g water) was added, followed by an additional hour of reaction at 80° C. The slightly opaque liquid was cooled to room temperature and used as seed polymer for a subsequent emulsion polymerization.

Preparation of an Acetal-functional Polyaddition Polymer Binder Dispersion

In a flask equipped with a mechanical stirrer, a nitrogen inlet and outlet, two dosing pumps, a thermocouple, a heating mantle, and a reflux condenser were placed 156.0 g of the seed copolymer described above and 0.5 g of sodium bicarbonate. The contents of the flask were heated to 80° C.

A monomer pre-emulsion was prepared by stirring 127.6 g of acetal monomer 3 described above, 64.1 g butyl acrylate, 15.6 g styrene, 1.0 g dodecyl mercaptan, 3.1 g Triton X-165, 1.7 g of sodium dodecyl sulphate, and 200 g water in an Erlenmeyer flask.

An initiator solution was prepared from 0.3 g ammonium persulphate and 30 g water. Dosing of the monomer pre-emulsion and the initiator solution to the polymerization flask was started simultaneously. The monomer addition was complete after 3 hours, while initiator dosing took 3.5 hours. The reaction temperature was kept at 80° C. throughout the addition phase and the mixture was stirred an additional hour at this temperature after completion of the initiator addition.

After cooling to room temperature a white, milky copolymer dispersion with solids content of 35.9 wt. % was obtained.

Preparation of a Thiol-functional Polyurethane Cross-linker Dispersion

A 4-neck flask was fitted with a variable speed stirrer, thermocouples in combination with a controller, a condenser, a nitrogen inlet and outlet, and a heating mantle. In the flask were placed 168.3 g of polyester diol 2 described above, 156.8 g of polyester diol 3 described above, 1 g of tin(II)octanoate, and 400 g tetrahydrofuran. The mixture was stirred at room temperature until homogeneous and 131.2 g of 4,4'-methylene-bis-(cyclohexyl isocyanate) (available from Bayer under the trademark Desmodur® W) were added over 30 minutes. The mixture exothermed to 30° C. and was further heated to 50° C. for 6 hours, after which time an isocyanate content of 1.84% was determined. The isocyanate-functional prepolymer was cooled to room temperature.

A 4-neck flask was fitted with a variable speed stirrer, thermocouples in combination with a controller, a condenser, a nitrogen inlet and outlet, and a heating mantle. In the flask were placed 44.8 g of trimethylol propane tris (3-mercaptopropionate), 2 g dimethyl ethanolamine, and 400 g tetrahydrofuran. 384.6 g of the isocyanate-functional prepolymer were added to the flask, with stirring, at room temperature over four hours. The mixture was stirred two more hours at room temperature and 25 g of acidic ion exchange resin DOWEX® 50WX4-200 (available from Dow Corning Corp., Michigan, USA) were added. The mixture was stirred for 15 minutes, after which time the ion exchange resin was removed by filtration. The resulting polymer solution was returned to the flask and heated to 45° C. The stirrer was set to the highest speed and 650 g water were added at a rate of 10 ml/min. When the addition of water was complete, a distillation head and a vacuum pump were connected to the flask, and the pressure was gradually lowered until all tetrahydrofuran was distilled off.

A white emulsion with the following characteristics was obtained: Solids content 23%, Mn 3,150, Mw 24,700, particle size 560 nm, and a thiol equivalent weight of 4,463 g/equivalent.

Preparation of N,N'-bis(4,4-diethoxybutyl)malonamide According to Formula X

A 4-neck flask was fitted with a variable speed stirrer, thermocouples in combination with a controller, a distillation column, a condenser, a nitrogen inlet and outlet, and a heating mantle. In the flask were placed 104.1 g diethyl malonate and 173.1 g aminobutyraldehyde diethyl acetal. The contents of the flask were heated to 140° C. with stirring and ethanol was distilled off. When the distillation ceased, the flask was connected to a vacuum line and the pressure was lowered to 200 mbar to remove the last traces of ethanol. The mixture was allowed to cool to room temperature. 217.3 g of a liquid with an amine number of 2.1 mg KOH/g were obtained, which corresponds to an amine conversion of 99.4%.

Coating Composition 1

Water borne coating based on acetal-functional polyurethane binder dispersion 1 and the thiol-functional polyurethane cross-linker dispersion A mixture of 20.6 g of acetal-functional polyurethane binder dispersion 1 and 22.3 g of the thiol-functional polyurethane cross-linker dispersion was prepared. The molar ratio of acetal-functional groups to thiol-functional groups was 1:1. To this mixture 2.3 g of a 10 wt. % aqueous solution of p-toluene sulphonic acid and 0.23 g of BYK® 346 (a wetting agent available from BYK-Chemie GmbH, Wesel, Germany) were added. The coating composition was applied to tin plates with a drawing bar and dried at room temperature. The following properties were obtained:

| | |
|---|---|
| Appearance: | OK |
| MEK resistance (1 day ageing): | 2 |
| MEK resistance (1 week ageing): | 2 |
| Water resistance (1 day ageing, 24 h exposure): | 4–5 |
| Persoz-hardness: | 52 s$^{-1}$ |

Coating Composition 2

Water borne coating based on acetal-functional polyurethane binder dispersion 2 and pentaerythritol tetrakis (3-mercapto propionate)

To 37.7 g of acetal-functional polyurethane binder dispersion 2 was added a mixture of 2.4 g pentaerythritol tetrakis (3-mercapto propionate) and 2.4 g ethyleneglycol monobutylether. During the addition the dispersion was stirred with an electric overhead stirrer at a speed of 300 rpm. The molar ratio of acetal-functional groups to thiol-functional groups was 1:2. Subsequently, 3.1 g of a 10 wt. % aqueous solution of p-toluene sulphonic acid were added. The coating composition was applied to, tin plates with a drawing bar and dried at room temperature. The following properties were obtained:

| | |
|---|---|
| Appearance: | OK |
| MEK resistance (1 day ageing): | 2–3 |
| MEK resistance (1 week ageing): | 3 |
| Water resistance (1 week ageing, 24 h exposure): | 3–4 |
| Persoz-hardness (1 day ageing): | 74 s$^{-1}$ |
| Persoz-hardness (1 week ageing): | 130 s$^{-1}$ |

Coating Composition 3

Water borne coating based on acetal-functional polyurethane binder dispersion 2 and pentaerythritol tetrakis (3-mercapto propionate)

To a mixture of 2.4 g pentaerythritol tetrakis (3-mercapto propionate) and 2.4 g ethyleneglycol monobutylether were added 37.7 g of acetal-functional polyurethane binder dispersion 2. During addition the dispersion was stirred with an electric overhead stirrer at a speed of 300 rpm. The molar ratio of acetal-functional groups to thiol-functional groups was 1:2. Subsequently, 3.1 g of a 10 wt. % aqueous solution of p-toluene sulphonic acid were added. The coating composition was applied to tin plates with a drawing bar and dried at room temperature. The following properties were obtained:

| | |
|---|---|
| Appearance: | OK |
| MEK resistance (1 day ageing): | 2–3 |
| MEK resistance (1 week ageing): | 3 |
| Water resistance (1 week ageing, 24 h exposure): | 3–4 |
| Persoz-hardness (1 day ageing): | 101 s$^{-1}$ |
| Persoz-hardness (1 week ageing): | 166 s$^{-1}$ |

Coating Composition 4

Water borne coating based on acetal-functional polyurethane binder dispersion 3 To 20 g of acetal-functional polyurethane binder dispersion 3, having molar ratio of acetal-functional groups to thiol-functional groups of 1:2, 1.4 g of a 10 wt. % aqueous solution of p-toluene sulphonic acid were added.

The coating composition was applied to tin plates with a drawing bar and dried at room temperature. The following properties were obtained:

| | |
|---|---|
| Appearance: | OK |
| MEK resistance (1 day ageing): | 5 |
| MEK resistance (1 week ageing): | 5 |
| Water resistance (1 week ageing, 24 h exposure): | 3 |
| Persoz-hardness (1 day ageing): | 263 s$^{-1}$ |
| Persoz-hardness (1 week ageing): | 286 s$^{-1}$ |

It can be concluded from the properties of the coatings obtained from coating compositions 2, 3, and 4 that acceptable properties can be obtained if the thiol-functional cross-linker is added to the acetal-functional polyurethane binder dispersion (see coating composition 2). When the order of addition is reversed, i.e. the acetal-functional polyurethane binder dispersion is added to a solution of the thiol-functional cross-linker, such as in coating composition 3, the resulting coating exhibits a higher hardness. When the acetal-functional polyurethane binder and the thiol-functional cross-linker are mixed prior to the formation of an aqueous dispersion, such as in coating composition 4, an even further increased hardness and an improved resistance of the coating to MEK are obtained.

Coating Composition 5

Solvent borne coating based on N,N'-bis(4,4-diethoxybutyl)malonamide and pentaerythritol tetrakis (3-mercapto propionate)

6.1 g of pentaerythritol tetrakis (3-mercapto propionate) and 8.4 g of N,N'-bis(4,4-diethoxybutyl)malonamide were mixed. The molar ratio of acetal-functional groups to thiol-functional groups was 1:1. To the mixture were added 2.9 g of a 10 wt. % solution of p-toluene sulphonic acid in a mixture of butyl acetate/2-propanol (weight ratio 95/5). The mixture was applied to tin plates with a drawing bar. The clear coat was cured and aged at room temperature.

The following properties were measured:

| | room temperature cure, 1 day ageing | room temperature cure, 2 weeks ageing |
|---|---|---|
| MEK resistance | 5 | 5 |
| Water resistance | 3 | 3 |
| Persoz hardness | Not determined | 52 s$^{-1}$ |

Coating Composition 6

Water borne coating based on the acetal-functional polyaddition polymer binder dispersion To 100 g of the acetal-functional polyaddition polymer binder dispersion described above was added 0.72 g of p-toluene sulphonic acid, and the mixture was applied to tin plates with a drawing bar. One sample was cured at room temperature. A second sample was allowed to dry 30 minutes at room temperature and subsequently cured at 60° C. for 60 minutes. The properties of this second sample were determined immediately after cooling to room temperature.

The following properties were measured:

| | room temperature cure, 1 day ageing | room temperature cure, 1 week ageing | 60 minutes cure at 60° C. |
|---|---|---|---|
| MEK resistance | 3–4 | 5 | 5 |
| Water resistance | 3 | 3 | 4 |

Coating Composition 7

Pigmented water borne coating based on acetal-functional polyurethane binder dispersion 2 and pentaerythritol tetrakis (3-mercapto propionate)

a) Preparation of a pigmented paste

To 95.6 g of a pigment mixture suitable for pigmentation of filler coatings were added with stirring 101.2 g of acetal-functional polyurethane binder dispersion 2. To the resulting mixture glass pearls were added and the pigments were dispersed with the aid of a high-speed dissolver at 7,000 RPM. Subsequently, a solution of 7.6 g pentaerythritol tetrakis (3-mercapto propionate) in 1.9 g methoxyproylacetate was stirred in. The resulting pigmented paste was diluted with an additional 27.9 g water and the glass pearls were filtered off.

b) Preparation of a pigmented coating composition

To 23.4 g of the pigmented paste described above were added 9.4 g of acetal-functional polyurethane binder dispersion 2, and a solution of 0.7 g pentaerythritol tetrakis (3-mercapto propionate) in 0.2 g methoxyproylacetate. During addition the dispersion was stirred with an electric overhead stirrer at a speed of 300 RPM. The molar ratio of acetal-functional groups to thiol-functional groups was 1:2. Finally, 2.0 g of a 10 wt. % aqueous solution of p-toluene sulphonic acid were added.

The coating composition was applied to steel plates with a drawing bar. The coating was allowed to dry 1 hour at room temperature, then baked in an oven at 60° C. for 30 minutes, and subsequently left at room temperature. The following properties were obtained:

| | |
|---|---|
| MEK resistance (1 day ageing): | 3 |
| MEK resistance (30 days ageing): | 4–5 |
| Water resistance (30 days ageing, 24 h exposure): | 4 |
| Persoz-hardness (1 day ageing): | 107 s$^{-1}$ |
| Persoz-hardness (30 days ageing): | 174 s$^{-1}$ |
| Dry adhesion (30 days ageing): | 10 |
| Wet adhesion (30 days ageing, 24 h immersion): | 10 |

The invention claimed is:

1. A coating composition comprising:
   a) an acetal-functional binder, and
   b) a thiol-functional cross-linker,
   wherein the acetal-functional binder is represented by formula II

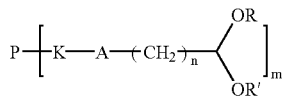

wherein
P is a binder backbone,
A is oxygen, sulphur or NR$^{VII}$, wherein R$^{VII}$ is hydrogen or an alkyl group with 1 to 4 carbon atoms,
K is a divalent and/or trivalent organic moiety having 1 to 30 carbon atoms, optionally comprising hydrogen, oxygen, nitrogen and/or sulphur atoms, and having one link to the binder backbone when K is divalent and two links to the binder backbone when K is trivalent, and wherein the individual moieties of K may be the same or different,
m is an integer from 1 to 50,
n is an integer from 1 to 10, and R and R' may be the same or different and represent alkyl groups with 1 to 4 carbon atoms.

2. The coating composition according to claim 1 wherein K is

3. The coating composition according to claim 1 wherein K is a divalent organic moiety comprising an —O-bond linked to the binder backbone and the individual moieties of K may be the same or different and are the moieties represented by (i) the structure of formula IIIa or (ii) the structure of formula IIIb,

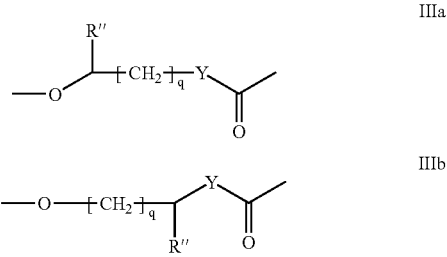

wherein
q is 0 or an integer from 1 to 4,
Y is oxygen or methylene, and
R" is hydrogen or an organic group having 1 to 30 carbon atoms, which organic group optionally may contain atoms and groups selected from oxygen, sulphur, nitrogen, hydroxyl, ester, ether, urethane, and amide.

4. The coating composition according to claim 1 wherein the binder is an acetal-functional polyurethane and wherein the individual moieties of K in formula II comprise di- and trivalent moieties, and the individual moieties of K are linked to the binder backbone via —O-bonds and are the moieties represented by (i) the structure of formula IIIa, (ii) the structure of formula IIIb, (iii) the structure of formula VIa or (iv) the structure of formula VIb

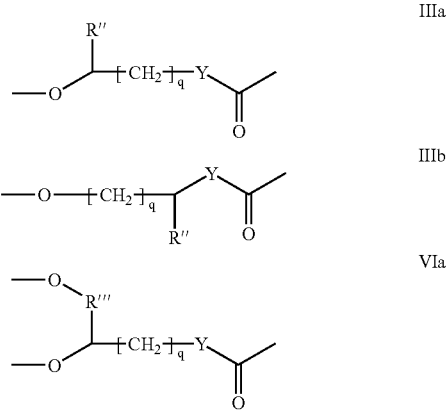

-continued

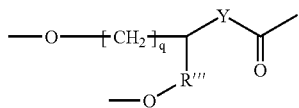

wherein q is 0 or an integer from 1 to 4,

Y is oxygen or methylene,

R" is hydrogen or an organic group having 1 to 30 carbon atoms, which organic group optionally may contain atoms and groups of oxygen, sulphur, nitrogen, hydroxyl, ester, ether, urethane or amide, and R'" is an alkylene group with 1 to 30 carbon atoms.

5. The coating composition according to claim 1 wherein the binder is an acetal-functional polyaddition polymer and wherein K is divalent and linked to the binder backbone via an —O-bond, and the individual moieties of K may be the same or different and are the moieties represented by (i) the structure of formula IXa or (ii) the structure of formula IXb,

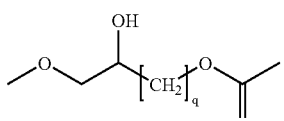

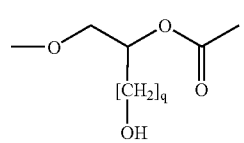

wherein q is 0 or an integer from 1 to 4.

6. The coating composition according to claim 2 wherein the acetal-functional binder is obtained obtained by amidation of esters with aminoacetals of formula Ia

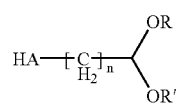

wherein n is an integer from 1 to 10,

A is $NR^{VII}$, wherein $R^{VII}$ is hydrogen or an alkyl group with 1 to 4 carbon atoms, and R and R' may be the same or different and represent alkyl groups with 1 to 4 carbon atoms.

7. The coating composition according to claim 6 wherein the acetal-functional binder is a compound represented by formula X

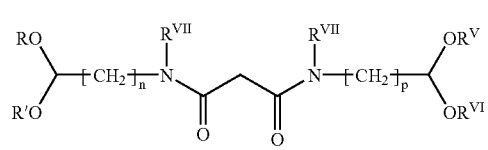

wherein n and p may be the same or different and represent integers from 1 to 10, R, R', $R^V$, and $R^{VI}$ may be the same or different and represent alkyl groups with 1 to 4 carbon atoms, and $R^{VII}$ is hydrogen or an alkyl group with 1 to 4 carbon atoms.

8. The coating composition according to claim 1 wherein the cross-linker is a thiol-functional polyurethane or esterification reaction product of a polyol and a mercapto carboxylic acid.

9. The coating composition according to claim 1 wherein the molar ratio of acetal-functional groups to thiol-functional groups is in the range between 1.0:0.1 and 1.0:3.5.

10. The coating composition according to claim 1 wherein the acetal-functional binder is a polyurethane or polyaddition polymer.

11. The coating composition according to claim 1 wherein the coating composition is solvent borne.

12. The coating composition according to claim 11 wherein the coating composition contains at most 10 weight-% of added organic solvent and which is liquid.

13. The coating composition according claim 1 wherein the coating composition is water borne.

14. A coated substrate, which has been coated with a composition according to claim 1.

15. A method of coating which comprises applying the coating composition according to claim 1 to a substrate, wherein the substrate is an automobile or a large transportation vehicle.

16. An adhesive composition comprising:
a) an acetal-functional binder, and
b) a thiol-functional cross-linker,
wherein the acetal-functional binder is represented by formula II

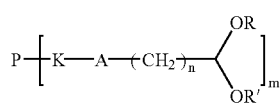

P is a binder backbone,

K is a divalent and/or trivalent organic moiety having 1 to 30 carbon atoms, optionally comprising hydrogen, oxygen, nitrogen or sulphur atoms, having one link to the binder backbone when K is divalent and two links to the binder backbone when K is trivalent, and the individual moieties may be the same or different, A is oxygen, sulphur or $NR^{VII}$, wherein $R^{VII}$ is hydrogen or an alkyl group with 1 to 4 carbon atoms, m is an integer from 1 to 50, n is an integer from 1 to 10, and R and R' may be the same or different and represent alkyl groups with 1 to 4 carbon atoms.

* * * * *